(12) United States Patent
Hwang et al.

(10) Patent No.: US 8,183,016 B2
(45) Date of Patent: May 22, 2012

(54) SYNTHESIS METHOD OF AROMATIC AMINO ACIDS

(75) Inventors: Tzann-Shun Hwang, Hsinchu (TW); Wei-Chun Cheng, Kaohsiung (TW); Hui-Chuan Fu, Taipei County (TW); Szu-Pei Wu, Hsinchu (TW)

(73) Assignee: I-Shou University, Kaohsiung County (TW)

( * ) Notice: Subject to any disclaimer, the term of this patent is extended or adjusted under 35 U.S.C. 154(b) by 159 days.

(21) Appl. No.: 12/707,220

(22) Filed: Feb. 17, 2010

(65) Prior Publication Data

US 2011/0003346 A1 Jan. 6, 2011

(30) Foreign Application Priority Data

Jul. 3, 2009 (TW) .............................. 98122547 A

(51) Int. Cl.
*C12P 13/04* (2006.01)
*C12P 21/00* (2006.01)
*C12N 15/00* (2006.01)
*C12N 1/21* (2006.01)
*C12N 9/10* (2006.01)
*C07K 14/00* (2006.01)
*C07H 21/00* (2006.01)

(52) U.S. Cl. .................... 435/106; 435/320.1; 435/69.1; 435/252.33; 435/193; 530/350; 536/23.2

(58) Field of Classification Search .................. 435/106, 435/69.1, 320.1, 252.33, 193; 530/350; 536/23.2
See application file for complete search history.

(56) References Cited

U.S. PATENT DOCUMENTS

| 4,497,964 A | 2/1985 | Ojima et al. |
| 5,010,175 A | 4/1991 | Rutter et al. |
| 5,705,660 A | 1/1998 | Berkowitz et al. |
| 7,163,917 B2 | 1/2007 | Zhao et al. |

OTHER PUBLICATIONS

Lo et al., Biotechnol. Prog. 21:411-415, 2005.*
Ahmad et al., Biotechnology Advances 27(3):286-296, May-Jun. 2009; available on-line Jan. 22, 2009.*
Nobe et al., The Journal of Biological Chemistry 273(45):29554-29564, 1998.*
Sergeeva et al., Plant Soil 297:1-13, 2007.*
Urrestarazu et al., Mol. Gen. Genet. 257:230-237, 1998.*

* cited by examiner

*Primary Examiner* — Delia Ramirez
(74) *Attorney, Agent, or Firm* — Muncy, Geissler, Olds & Lowe, PLLC

(57) ABSTRACT

A method for synthesizing aromatic amino acids according to one aspect of the present invention includes processes of: (a) of preparing a thermostable a *Thermus thermophilus* aspartate aminotransferase by culturing an *E. coli* BL21(DE3) cell transformed with a vector comprising a gene encoding the *Thermus thermophilus* aspartate aminotransferase; (b) contacting the thermostable *Thermus thermophilus* aspartate aminotransferase of (a) with an amino donor and an amino acceptor at a temperature range of 50-80° C. to obtain an aromatic amino acid; (c) precipitating the aromatic amino acid of (b); and (d) recovering the thermostable *Thermus thermophilus* aspartate aminotransferase.

7 Claims, 4 Drawing Sheets

SEQUENCE LISTING

<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: Synthetic oligonucleotide primer
      Fwd. Primer TtAspAT-1

<400> SEQUENCE: 1
acttagcata tgcgcggcct ttccc                                              25

<210> SEQ ID NO 2
<211> LENGTH: 28
<212> TYPE: DNA
<213> ORGANISM: Artificial Sequence
<220> FEATURE:
<223> OTHER INFORMATION: Synthetic oligonucleotide primer
      Rev. Primer TtAspAT-2

<400> SEQUENCE: 2
cccacgaccc cgcgcggttc gaacccaa                                           28

SYNTHESIS METHOD OF AROMATIC AMINO ACIDS

BACKGROUND OF THE INVENTION

1. Field of the Invention

The present invention relates to a method for synthesizing aromatic amino acids, more particularly, to a method for synthesizing homophenylalanine in a thermostable and easy process.

2. Description of the Related Art

Hypertension, also called high blood pressure, means patient's blood pressure higher than normal standard. Severely high pressure is defined as 50% or over 50% higher than standard. Persistent hypertension might lead to strokes, heart attacks, heart failure and arterial aneurysm. In industrialized countries, hypertension is a main reason of cardiovascular morbidity and mortality.

Renin-Angiotensin system (RAS) is a crucial moderating factor for blood pressure. In the RAS reaction, Angiotensin-Converting Enzyme (ACE), which is a circulating enzyme for mediating extracellular volume and arterial vasoconstriction, has two primary functions: (1) catalyzing the conversion of angiotensin I to angiotensin II as a vasoconstrictor in a substrate concentration dependent manner, and (2) catalyzing the degradation of a vasodilator-bradykinin. Therefore, ACE is a good target for medicines to therapy some multiple failures including high blood pressure, heart failure, diabetic nephropathy and type 2 diabetes mellitus. Angiotensin-Converting Enzyme Inhibitors (ACEIs) can inhibit the activity of ACE, decreasing the formation of angiotensin II and the degradation of bradykinin. Therefore, ACEIs have been used to prevent over-activation of the RAS, which leads to a systematic dilation of blood vessels and lower blood pressure. One of the raw materials for synthesizing ACEIs is homophenylalanine (HPA). HPA is sorted into a D-form homophenylalanine ($_D$-HPA) and a L-form homophenylalanine ($_L$-HPA). Due to its slow metabolism and tendency to remain in organisms, the safety and medicines' kinetics of the $_D$-HPA needs further evaluation. Consequently, most medicines of ACEIs use $_L$-HPA as a raw material, such as Enalapril, Ramipril, Quinapril and Lisinopril. HPA is not a natural occurred amino acid and can be synthesized artificially. The conventional synthesis methods of amino acids includes an enantioseletive hydrogenation method, a full chemical synthesis method and a biochemical synthesis method.

The enantioseletive hydrogenation method uses organic solvents to extract $_D$-HPA and $_L$-HPA from a kinetic resolution. Sequentially, $_D$-HPA can be isolated by different optical activity, but the $_D$-HPA is not a good raw material for current ACEIs. Therefore, the synthetic HPA by the enantiotioselective hydrogenation method is limited.

The full chemical synthesis method is widely used in pharmaceutical industries for massive synthesis of aromatic amino acids. The full chemical synthesis method uses an intermediate product beta-benzoylacrylic acid with 1-arylethylamine to synthesize HPA through a reduction. However, the product of HPA includes $_D$-HPA and $_L$-HPA so that an additional separation is required to separate $_D$-HPA and $_L$-HPA. The full chemical synthesis method for HPA is complicated and uses many kinds of chemicals and organic solvents, usually leading to high cost and environmental pollution.

The biochemical synthesis method is a biotransformation method in which an aminotransferase is used as a biocatalyst to selectively synthesize stereospecific amino acids. The biochemical synthesis method has some advantages, such as being simple to synthesize stereospecific amino acids and using few chemicals and low environmental pollution. A previous report showed that an *E. coli* aspartate aminotransferases can be used to synthesize $_L$-HPA. It uses an aspartate as an amino donor and an 2-oxo-4-phenylbutyric acid (OPBA) as an amino acceptor in the amino-transferring reaction at 37° C. However, *E. coli* aspartate aminotransferase has following defects in synthesizing $_L$-HPA.

First of all, the efficiency in synthesizing amino acid by the biochemical synthesis method is low. A higher temperature leads to a higher reaction rate, but *E. coli* aspartate aminotransferase is less stable, and easily becomes inactive over 37° C. or after hours of working time. Hence, the *E. coli* aspartate aminotransferase reaction cannot be carried out at a higher temperature. Moreover, even if the *E. coli* aspartate aminotransferase reaction is carried out at 37° C., the *E. coli* aspartate aminotransferase easily becomes inactive after few hours. Therefore, a large amount of *E. coli* aspartate aminotransferase or a time-consuming process is required to synthesize amino acids by the biochemical synthesis method. On the other hand, a lower reaction temperature also causes a lower solubility of aromatic amino acceptors, and accordingly a lower efficiency in amino acids synthesizing reaction is obtained. Next, the cost of the biochemical synthesis method is high. *E. coli* aspartate aminotransferase easily becomes inactive over 37° C., so that coolers or freezers are required for its preparation, storage and also for its transportation. The enzyme activity of *E. coli* aspartate aminotransferase will be decreased if proper procedures are not taken in the preparation, storage and transportation. Thus, a high cost is required to obtain active *E. coli* aspartate aminotransferase.

SUMMARY OF THE INVENTION

An objective of the present invention is to provide a method for synthesizing aromatic amino acids which can be processed at a high temperature for a shorter time and with higher efficiency.

Another objective of present invention is to provide a method for synthesizing aromatic amino acids by using a thermostable and easily-stored aminotransferase, so that the amount of aminotransferase needed in reaction and the cost in manufacturing are low.

A method for synthesizing aromatic amino acids comprising the processes of:

(a) preparing a thermostable *Thermus thermophilus* aspartate aminotransferase (TtAspAT) by culturing an *E. coli* BL21(DE3) cell transformed with a vector comprising a gene encoding the *Thermus thermophilus* aspartate aminotransferase; (b) contacting the thermostable *Thermus thermophilus* aspartate aminotransferase of (a) with an amino acid donor and an amino accepter at a temperature range of 50° C. and 80° C. to obtain an aromatic amino acid; (c) precipitating the aromatic amino acid of (b); and (d) recovering the thermostable *Thermus thermophilus* aspartate aminotransferase; wherein, the process of (a) further comprising steps of: isolation, by PCR of the amplified thermostable TtAspAT gene from desired organism's genomic DNA with specific primer pairs being set forth in SEQ ID NO. 1 and 2; construction, by constructing the amplified thermostable TtAspAT gene in an expression vector; and transformation, by transforming the expression vector into a host for expressing the thermostable TtAspAT.

Further scope of the applicability of present invention will become apparent from the detailed description given hereinafter. However, it should be understood that the detailed description and specific examples, while indicating preferable embodiments of the invention, are given by way of illustration only, since various will become apparent to those skilled in the art from this detailed description.

BRIEF DESCRIPTION OF THE DRAWINGS

The illustrative embodiments may best be described by reference to the accompanying drawings where.

Figure 1:
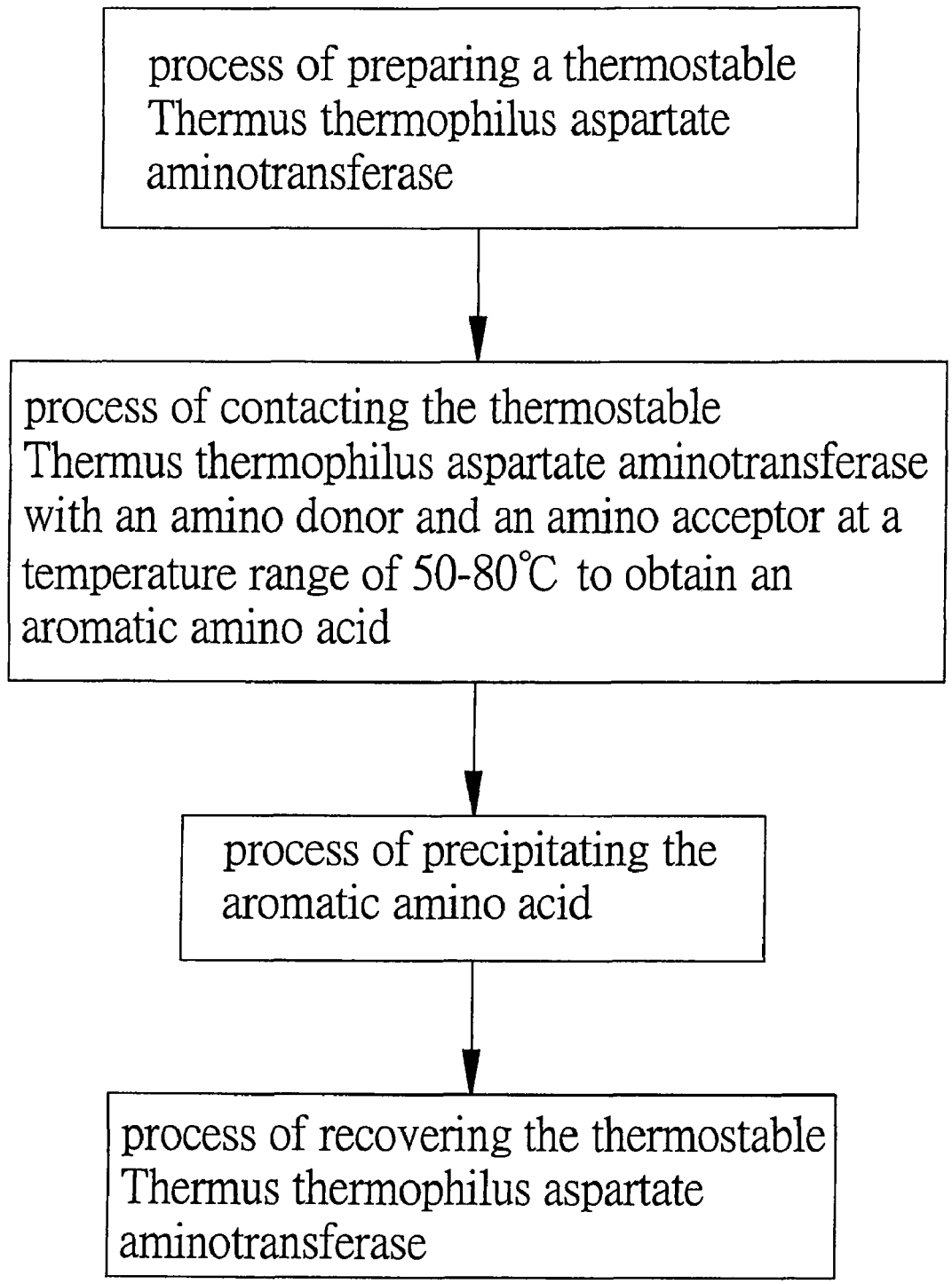
FIG. 1 shows a flowchart of the method for synthesizing aromatic amino acids in accordance with the present invention.

All figures are drawn for ease of explanation of the basic teachings of the present invention only; the extensions of the figures with respect to number, position, and relationship, of the parts to form the preferred embodiments will be explained or will be within the skill of the art after the following teachings of the present invention have been read and understood. Further, the exact dimensions and dimensional proportions to conform to specific force, weight, strength, and similar requirements will likewise be within the skill of the art after the following teachings of the present invention have been read and understood.

Where used in the various figures of the drawings, the same numerals designate the same or similar parts. Furthermore, when the terms "S1", "S2", "S3", and similar terms are used herein, it should be understood that these terms have reference only to the structure shown in the drawings as it would appear to a person viewing the drawings and are utilized only to facilitate describing the invention.

DETAILED DESCRIPTION OF THE INVENTION

Referring to FIG. 1, the method for synthesizing aromatic amino acids of present invention comprises three processes of: preparing thermostable *Thermus thermophilus* aspartate aminotransferase by culturing an *E. coli* BL21(DE3) cell transformed with a vector comprising a gene encoding the *Thermus thermophilus* aspartate aminotransferase; (b) contacting the thermostable *Thermus thermophilus* aspartate aminotransferase of (a) with an amino donor and an amino acceptor at a temperature range of 50-80° C. to obtain an aromatic amino acid; (c) precipitating the aromatic amino acid of (b); and (d) recovering the thermostable *Thermus thermophilus* aspartate aminotransferase. The process of (a) produces a massive amount of *Thermus thermophilus* aspartate aminotransferase (TtAspAT) by using gene cloning techniques, which comprises the steps of: isolation, by a PCR amplified thermostable TtAspAT gene from the desired organism's genomic DNA with specific primer pairs being set forth in SEQ ID NO. 1 and 2; construction, by constructing the amplified thermostable TtAspAT gene in an expression vector; and transformation, by transforming the expression vector into a host for expressing the thermostable TtAspAT. The process (b) performs a TtAspAT-catalyzing reaction, in which an amino group from an amino donor is transferred to the carbonyl group of a keto acid (an amino acceptor) for producing amino acids. The process of (c) recovers and purifies synthesized amino acids, and recycles the active aminotransferase in the supernatant from a reaction mixture.

The process (a) provides a thermostable and easy-purifying aspartate aminotransferase (AspAT), which is a product by expressing the TtAspAT (*Thermus thermophilus* aspartate aminotransferase) gene in *E. coli*. The construction of TtAspAT gene in an *E. coli* expression vector with binding tag is obtained by recombinant gene cloning techniques, which is well known to persons skilled in the art. In the step of isolation, a target DNA (TtAspAT gene) was amplified from desired organism's genomic DNA. In the step of construction, the amplified TtAspAT gene was constructed into an appropriate vector for protein expression in suitable host. In the step of transformation the expression vector is transformed into a host for expressing the thermostable TtAspAT. Polymerase chain reaction (PCR) is the most commonly used technique for amplifying specific sequences. In the step of isolation, the PCR reaction is performed by preparing the target DNA from a genomic DNA sample, unwinding the two strands thereof, hybridizing the unwound strands with primers, and amplifying the target DNA (TtAspAT) with DNA polymerase. The oligonucleotide sequences used as primers can be optional modified in part, for example, to introduce endonuclease restriction site or eliminate stop codon for fusing to downstream sequences. The sequence information of TtAspAt gene can be obtained directly from GenBank and used to design primers which make the construction fused to a suitable tag in the C-terminal of the recombinant TtAspAT. To simplify the work, the tag chosen in this invention is 6× histidine tag, which can bind to Ni-chelating resin to facilitate purification of the expressed recombinant TtAspAT. In a preferred embodiment, genomic DNA is prepared from *Thermus thermophilus* and TtAspAT gene is amplified from the genomic DNA by the PCR technique. Normally, the expression vector can be chosen by those skilled in the art as desired. After proper manipulations by gene cloning techniques, which is well known to persons skilled in the art, a construction with the DNA sequence of 6× histidine tagged TtAspAT can be obtained. The construction (vector DNA with TtAspAT gene) can be transformed in to suitable host for protein expression. Protein expression and purification for TtAspAT preparation are performed by processes well known in the art.

In the process of (b) in the present invention, the amino donor is L-aspartate and the amino acceptor can be selected from α-ketoglutarate (α-KG), homophenylpyruvate, phenylpyruvate, indole-3-pyruvic acid or p-hydroxyphenylpyruvate individually. The TtAspAT can transfer an amino group from the L-aspartate to a carbonyl group of a-KG, homophenylpyruvate, phenylpyruvate, indole-3-pyruvic acid or p-hydroxyphenylpyruvate to generate $_L$-HPA, L-phenylalanine, L-tryptophan and L-tyrosine respectively. An advantageous condition for the process of (a) is that it is sufficient to be processed at a temperature between 50° C. and 80° C., preferably at 70° C. for 30 to 90 minutes. The preferred embodiment of the present invention is that the TtAspAT transfers the amino group from L-aspartate to the carbonyl group of homophenylpyruvate to generate $_L$-HPA. The synthesized $_L$-HPA can be further put to use in a synthesis of ACEI as a raw material of ACEI.

Figure 4:
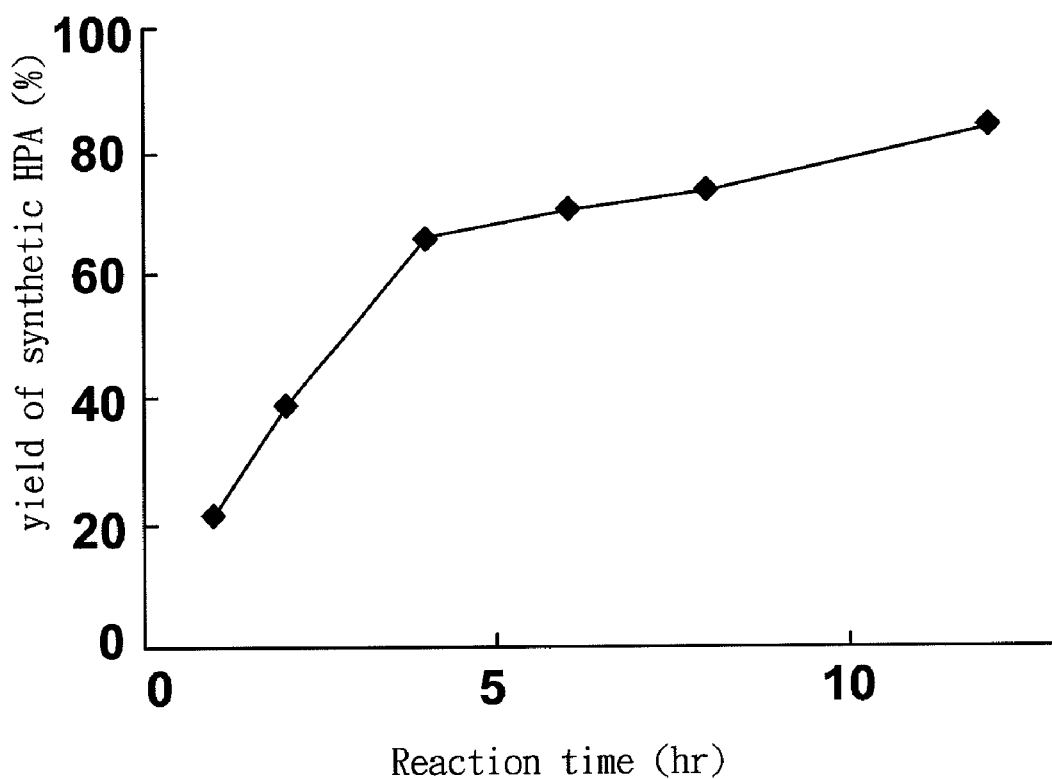
FIG. 4 shows a linear chart illustrating reaction time and yield of synthesized HPA in accordance with the present invention.

In a TtAspAT activity test, high performance liquid chromatography (HPLC) is used to examine the concentration of synthesized $_L$-homophenylalanine ($_L$-HPA). According to FIG. 4, the yield of $_L$-HPA reaches a peak after 6 hours of reaction time. Hence, $_L$-HPA can be purified after 6 hours of reaction time, followed by recycling active aminotransferase after the reaction for further use in another cycle of $_L$-HPA synthesis.

After the synthesis of $_L$-HPA, the product, namely $_L$-HPA was precipitated by turning down the temperature of reaction and followed by recycling the active aminotransferase from a supernatant of reactant. In the present invention, a higher temperature is provided for catalyzing reaction, so as to enhance the activity of TtAspAT, to promote the solubility of the substrates and to advance the synthesis of amino acids. Therefore, the synthesized $_L$-HPA was easily precipitated from the reactant in the process of (c) by maintaining a temperature of 0 degree centigrade in an ice-water bath. Moreover, the supernatant of the reactant still has high aminotransferase activity after amino-transferring reaction (see the half life test in the process of (b)). As a result, the supernatant can be recycled 2-3 times at least for recycling aminotransferase. L-phenylalanine, L-tryptophan and L-tyrosine synthesized in the process of (b) are hydrophobic compounds, needing to be extracted through organic solvents, followed by preparative C18 column chromatography for the HPLC isolation.

As has been discussed above, the TtAspAT can catalyze the synthesis of aromatic amino acids at a high temperature between 50° C. and 80° C., so as to increase the solubility of amino donors and amino acceptors. With the performance of the TtAspAT, the reaction time for synthesizing aromatic amino acids can be significantly reduced and the efficiency in synthesizing aromatic amino acids can be increased. Moreover, the TtAspAT is thermostable, which makes the TtAspAT easy to store and transport at room temperature. Furthermore, the TtAspAT is more active at a higher temperature. Therefore, a smaller amount of the TtAspAT can be used to more efficiently synthesize amino acids in the method of present invention through a time-saving and less-costly process.

Although the invention has been described in detail with reference to its presently preferable embodiment, it will be understood by one of ordinary skill in the art that various modifications can be made without departing from the spirit and the scope of the invention, as set forth in the appended claims.

EXAMPLES

Example 1

Preparation of Recombinant *Thermus thermophilus* Aspartate Aminotransferase by Gene Cloning Isolation of genomic DNA from *Thermus thermophilus*

A *Thermus thermophilus* used in the invention was bought from Bioresource collection and research center (BCRC), Hsinchu, Taiwan. The genomic DNA of *Thermus thermophilus* was isolated according to the method as described by Sambrook et al. 1989. The *Thermus thermophilus* was incubated in a 10 ml *Thermus* medium at 60° C. overnight. The *T. thermophilus* was harvested by centrifuging 5 ml of the overnight culture at 14,000 rpm for 30 seconds. Removing the supernatant and adding 377 µl of 50 mM TrisHCl (pH8.0) to suspend the pellet. Then 2 µl of proteinase K (20 mg/ml) and 20 µl of 10% SDS was added, mixed well and incubated at 37° C. for 1 hour. The treated mixture was then added with 95 µl of 4.1 M NaCl and 55 µl of 10% CTAB sequentially and incubated at 65° C. for 10 minutes. TrisHCl buffer-saturated phenol was used to extract the mixture once. Transfer the supernatant to a new microcentrifuge tube, and phenol-chloroform solution (1:1) was used to extract the mixture one more time. Transfer the supernatant to a new microcentrifuge tube, adding 330 µl isopropanol and inverts several times to precipitate a genomic DNA of *T. thermophilus*. Wash the precipitated genomic DNA of *T. thermophilus* with 70% ethanol for 3 times and dry it. Finally the precipitated genomic DNA of *T. thermophilus* was resuspended in 50 µl water.

Primer Design and Polymerase Chain Reaction (PCR)

Two primers, TtAspAT-F and TtAspAT-R, were designed based on the sequence of the TtAspAT gene of *T. thermophilus* HB8. The sequence of the forward primer TtAspAT-F is (5'-ACTTAGCATATGCGCGGCCTTTCCC-3') SEQ ID NO: 1 and of the reverse primer TtAspAT-R(5'-CCCACGAC-CCCGCGCGGTTCGAACCCAA-30 SEQ ID NO: 2 to amplify TtAspAT gene. A PCR reaction mixture (50 µl) contained 1 µl of genomic DNA of *T. thermophilus* as template, 5 µl of 10× buffer, 4 µl of dNTP (2.5 mM), 1 µl of primer TtAspAT-F (1 pmole/µl), 1 µl of primer TtAspAT-R (1 pmole/µl), 1 µl of DNA polymerase and 40 µl water was prepared. The PCR reaction mixture was put into a thermocycler to perform PCR reaction in 40 cycles to amplify the TtAspAT gene.

Cloning of TtAspAT Gene into Expression Vector

A plasmid pET21b and the fragment of TtAspAT gene amplified by PCR were digested with two restriction endonucleases (NdeI and HindIII) and ligated by a T4 DNA ligase at 16° C. for 12 hours to obtain a ligated DNAs. The ligated DNAs were transformed into an *E. coli* DH5a to select clones with correct insert, and then a correct clone was transformed into *E. coli* BL21(DE3) for massive express TtAspAT.

Protein Expression and Purification

*E. coli* BL21(DE3) harboring the TtAspAT gene was incubated in a LB broth containing 100 µl/ml ampicillin at 37° C. overnight and then subcultured until the $OD_{600}$ of a culture reached 0.6. Then isopropyl-β-D-thiogalactopyranoside (IPTG) was added to final concentration of 1 mM and incubated for another 18 hours for induction. The culture was harvested by centrifugation at 7,500 rpm for 10 minutes at 4° C. to obtain a pellet. After washing the pellet with 0.9% NaCl, the pellet was resuspended in a PLP buffer (1 mM PLP in 0.1 M TrisHCl buffer, pH 8.0) and disrupted by ultra-sonication. The suspension was then centrifuged at 13,000 rpm for 20 minutes at 4° C. to remove the cell debris and clear supernatant was used as a crude extract. The crude extract was heated at 60° C. water bath for 20 minutes and centrifuged at 13,000 rpm for 20 minutes at 4° C. to remove the denatured proteins. The clear supernatant was subjected to a Ni-chelating resin column for further purification by one-step chromatography, since the recombinant TtAspAT contains six histidine tagged in C-terminal which can bind to Ni-chelating resin and be simple eluted by imidazole solution to obtain *Thermus thermophilus* aspartate aminotransferase (TtAspAT).

Example 2

Enzyme Assay in Different Conditions

Figure 2:
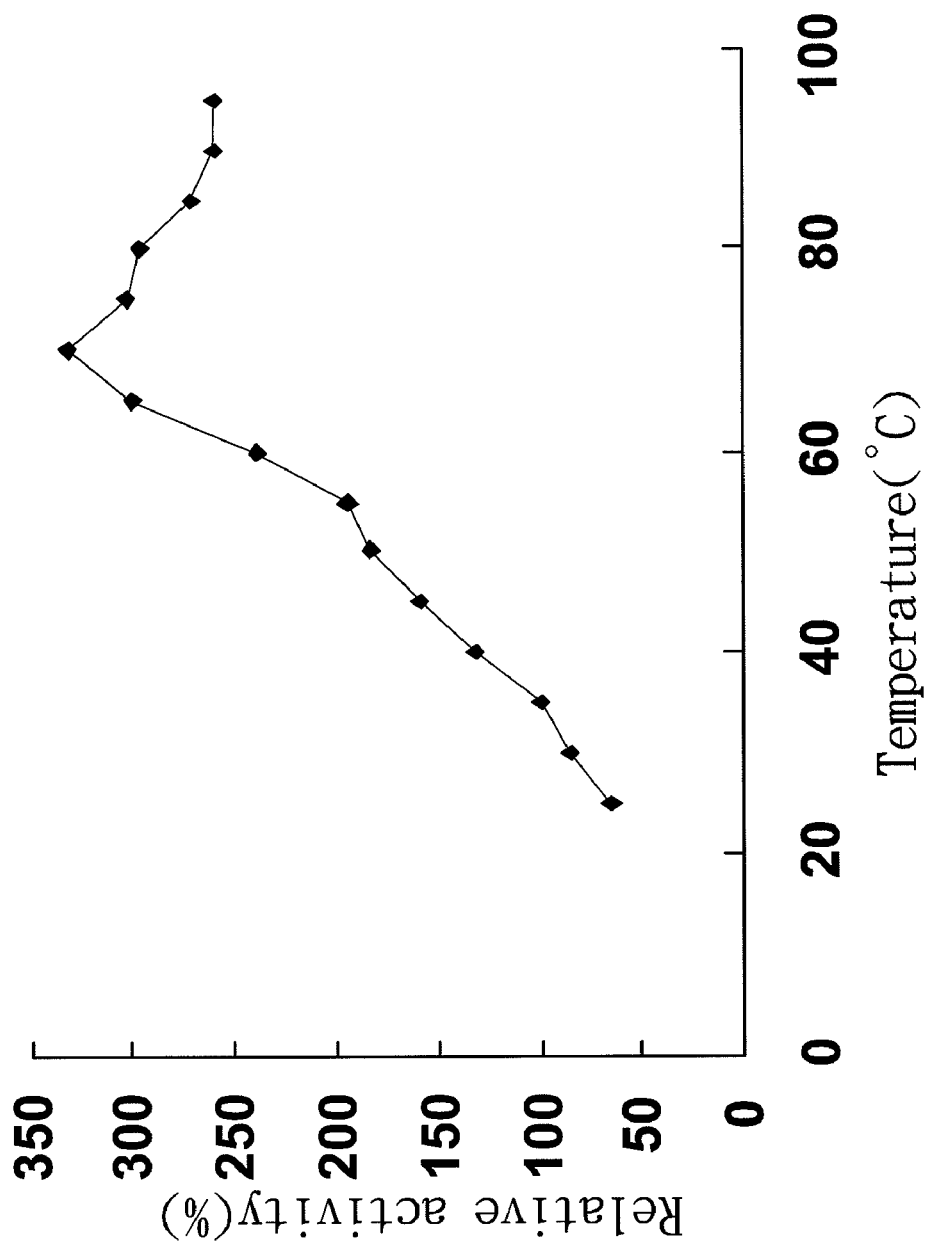
FIG. 2 shows a linear chart illustrating temperature and relative activity of TtAspAT in accordance with the present invention.

This activity of TtAspAT was determined by a modified malate dehydrogenase (MDH) coupling method (Ziehr, H. and M. R. Kula, 1985). A mixture contained 200 mM L-aspartate, 25 mM a-KG, 0.15 mM NADH, 0.1 mM PLP, 5 U of MDH, and 100 mM TrisHCl buffer (pH 8.0), was prepared in a total volume of 1 ml. The reaction was initiated by adding a diluted TtAspAT and proceeded at specific temperature. The decrease of absorbance at 340 nm due to consumption of NADH was monitored for 3-5 minutes and was then converted to enzyme activity. One unit of enzyme activity was defined as the amount of enzyme that catalyzed the production of oxaloacetate equal to 1 µmole NADH consumed for converting oxaloacetae to malate per minute. The preferred embodiment of the present invention examines the optimal catalysis temperature and stability of TtAspAT The TtAspAT activity in different temperature was determined under standard reaction mixture in every 5° C. increased temperature by MDH-coupling method. The enzymatic activity was measured from 25° C. to 95° C. (Table1), the related results are illustrated in FIG. 2. The TtAspAT activity reached the highest activity at 70° C. and decreased over 70° C. Thereof the optimal temperature of TtAspAT activity is 70° C.

TABLE 1

TtAspAT activity in different reaction temperature

| Temperature (° C.) | Specific activity (U/mg)[a] | Relative activity (%) |
|---|---|---|
| 25 | 70.77 | 65 |
| 30 | 93.28 | 85 |
| 35 | 109.37 | 100 |
| 40 | 144.75 | 132 |
| 45 | 174.34 | 159 |
| 50 | 200.08 | 183 |
| 55 | 212.30 | 194 |
| 60 | 262.48 | 240 |
| 65 | 328.10 | 300 |
| 70 | 362.83 | 332 |
| 75 | 331.96 | 304 |
| 80 | 324.24 | 296 |
| 85 | 297.22 | 272 |
| 90 | 283.72 | 259 |
| 95 | 283.72 | 259 |

[a]One unit of enzyme activity was defined as the amount of enzyme that produced the oxaloacetate equal to 1 μmole NADH consumed for converting oxaloacetae to malate per minute.

Figure 3:
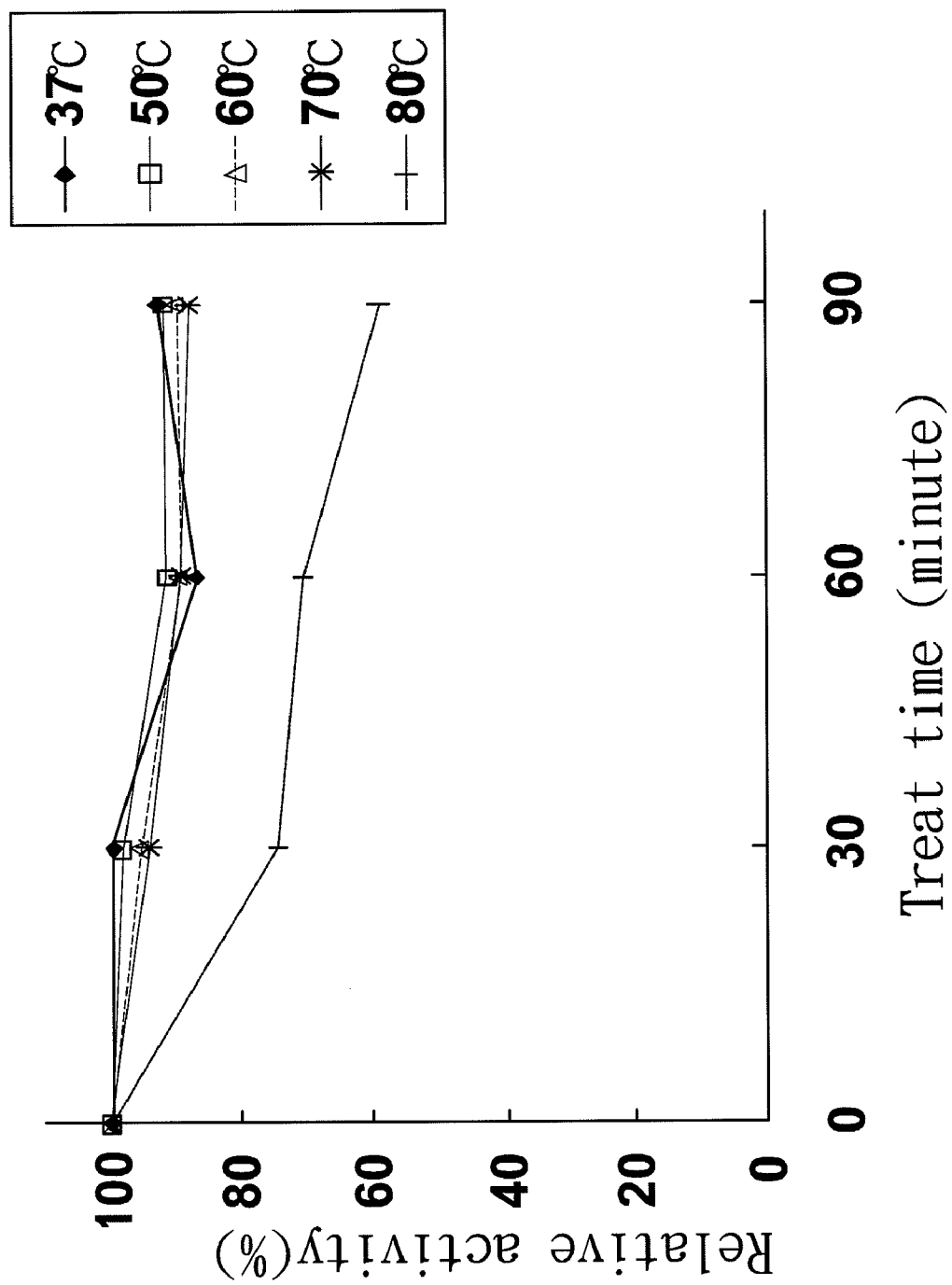
FIG. 3 shows a linear chart illustrating treat time and relative activity of TtAspAT in different temperature in accordance with the present invention.

The stability of TtAspAT was measured by the way that the enzyme was conducted a heat treatment at 37° C., 50° C., 60° C., 70° C. and 80° C. for a period of time. After the heat treatment, MDH-coupling method was used to determine the remaining activity of the heat-treated TtAspAT. By plotting treating time to the remaining activity of TtAspAT (illustrated in FIG. 3), the decrease rates of the TtAspAT activity were observed at different temperature and the slope was calculated in regression analysis to estimate the half life of TtAspAT at a specific temperature. The TtAspAT activity was shown to have the highest stability when it was subjected to the heat treatment at 50° C. (Table2) However, considering both that the highest activity was at 70° C. and the highest stability was at 50° C., a compromised condition is set at 60° C. in this invention to have better activity and better stability for proceeding following amino-transferring reaction to obtain the better production and better recycling of TtAspAT with less inactive effect, which means it can active longer and can be use to react more times.

TABLE 2

The half-life of TtAspAT incubated in different temperature

| Temperature (° C.) | Half-life (hours) |
|---|---|
| 37 | 14.3 |
| 50 | 16.0 |
| 60 | 14.1 |
| 70 | 12.1 |
| 80 | 3.8 |

Example 3

High Performance Liquid Chromatography (HPLC) Analysis of TtAspAT Activity Against Homophenylpyruvate The high performance liquid chromatography (HPLC) analysis of TtAspAT against homophenylpyruvate was performed by the method modified from Houng, J. Y. and C. L. Hsieh (1996, U.S. Pat. No. 5,552,317). A reaction mixture contained 200 mM aspartate, 25 mM homophenylpyruvate, 100 mM Tris-HCl buffer (pH8.0), 5 U of TtAspAT in a final reaction volume of 1 ml was prepared. The reaction mixture was aliquoted into 0.12 ml for each microtube and incubated at 60° C. for 1, 2, 4, 6, 8 and 12 hours individually. Reaction was stopped by adding 35 μl, 1 of 6N HCl. The amount of homophenylalanine (HPA) produced by TtAspAT catalyzed bioconversion was then measured by the HPLC using a reverse phase C18 column (Ascentis C18, 250 mm×4.6 mm, particle size 5 μm, SUPELCO, PA). The mobile phases were an A solvent contained 10% methanol/perchloric acid (pH 2.0) and a B solvent contained 80% methanol/perchloric acid (pH 2.0). The flow rate was set at 0.7 ml/min. The gradient was set from 0% to 100% of the B solvent. HPA of the concentration 0.5 mM, 1 mM, 1.5 mM and 2 mM was used to set standard curve. The yield of the bioconversion reaction was calculated by the total amount of produced HPA divided with the amount of inputted HPP. The HPLC analysis showed that the yield after 6 hours slowed down and reached 83.42% after 12 hours reaction. (Table 3) The relationship between reaction time and yield of the HPA (illustrated in FIG. 4) showed that the yield reached the boundary of the plateau after 6 hours. Since HPA is easy to precipitated by lowing temperature, the reaction is not necessary to proceed longer time to get better yield and the active enzyme can be recycled and used for another batch of synthesis. Thus, time and cost of synthesis amino acids can be saved.

TABLE 3

The yield of homophenylalanine (HPA) in the bioconversion catalyzed by TtAspAT

| Time (hours) | Yield (%) |
|---|---|
| 1 | 21.14 |
| 2 | 38.47 |
| 4 | 65.53 |
| 6 | 70.33 |
| 8 | 73.22 |
| 12 | 83.42 |

What is claimed is:

1. A method for synthesizing aromatic amino acids comprising the steps of:
   (a) isolating a gene encoding a thermostable *T. thermophilus* aspartate aminotransferase by PCR amplification using *T. thermophilus* genomic DNA and the primer pair set forth in SEQ ID NO: 1 and 2;
   (b) inserting the *T. thermophilus* aspartate aminotransferase gene obtained in step (a) in an expression vector;
   (c) transforming an *E. coli* BL21 (DE3) cell with the expression vector of step (b);
   (d) culturing the transformed *E. coli* BL21 (DE3) cell of step (c) to produce the thermostable *T. thermophilus* aspartate aminotransferase;
   (e) contacting the thermostable *T. thermophilus* aspartate aminotransferase of step (d) with an amino donor and an amino acceptor at a temperature range of 50-80° C. to obtain an aromatic amino acid;
   (f) precipitating the aromatic amino acid of (e); and
   (g) recovering the thermostable *T. thermophilus* aspartate aminotransferase.

2. The method for synthesizing aromatic amino acids as defined in claim 1, wherein the process of contacting is carried out at 70° C.

3. The method for synthesizing aromatic amino acids as defined in claim 1, wherein the process of contacting is carried out for 6 hours.

4. The method for synthesizing aromatic amino acids as defined in claim 1, wherein the synthesized aromatic amino acid is homophenylalanine and wherein the *T. thermophilus* aspartate aminotransferase uses aspartate as an amino donor and homophenylpyruvate as an amino acceptor.

5. The method for synthesizing aromatic amino acids as defined in claim 4, wherein the synthesized homophenylalanine is precipitated at a temperature of 0° C.

6. The method for synthesizing aromatic amino acids as defined in claim 1, wherein the synthesized aromatic amino acid is phenylalanine and wherein the *T. thermophilus* aspartate aminotransferase uses aspartate as an amino donor and phenylpyruvate as an amino acceptor.

7. The method for synthesizing aromatic amino acids as defined in claim 6, wherein the synthesized phenylalanine is purified by high performance liquid chromatography (HPLC) or extracted with organic solvents.

* * * * *